United States Patent
Hu

(10) Patent No.: US 7,348,441 B2
(45) Date of Patent: Mar. 25, 2008

(54) METHYL 2,4,9-TRITHIAADAMANTANE-7-CARBOXYLATE

(75) Inventor: Jun Hu, Fairlawn, OH (US)

(73) Assignee: The University of Akron, Akron, OH (US)

( * ) Notice: Subject to any disclaimer, the term of this patent is extended or adjusted under 35 U.S.C. 154(b) by 0 days.

(21) Appl. No.: 10/562,090

(22) PCT Filed: Jul. 1, 2004

(86) PCT No.: PCT/US2004/021558

§ 371 (c)(1),
(2), (4) Date: Mar. 6, 2007

(87) PCT Pub. No.: WO2005/120186

PCT Pub. Date: Dec. 22, 2005

(65) Prior Publication Data

US 2007/0173650 A1    Jul. 26, 2007

(51) Int. Cl.
*C07D 339/00* (2006.01)
(52) U.S. Cl. ....................................... 549/20
(58) Field of Classification Search ................... 549/20
See application file for complete search history.

(56) References Cited

U.S. PATENT DOCUMENTS

| | | |
|---|---|---|
| 3,719,710 A | 3/1973 | Thomas et al. |
| 4,033,982 A | 7/1977 | Hay |
| 4,202,892 A | 5/1980 | Weiner et al. |
| 4,474,970 A | 10/1984 | Dirlikov |
| 4,663,416 A | 5/1987 | Dirlikov |
| 5,045,551 A | 9/1991 | Chandraratna |
| 5,164,491 A | 11/1992 | Froehler et al. |
| 5,204,455 A | 4/1993 | Froehler et al. |
| 5,977,400 A | 11/1999 | DeWitt et al. |
| 6,300,486 B1 | 10/2001 | Froehler et al. |

OTHER PUBLICATIONS

Kittredge et al. Helvetica Chimica Acta (2002), 85(3), 788-798.*

* cited by examiner

*Primary Examiner*—D. Margaret Seaman
*Assistant Examiner*—Nizal S. Chandrakumar
(74) *Attorney, Agent, or Firm*—Roetzel & Andress, L; George W. Moxon II

(57) ABSTRACT

Methyl 2,4,9-trithiaadamantane-7-carboxylate and a method for its manufacture is disclosed. The method reacts oxidized methyl triallyl acetate with a Lewis acid and a sulphuring agent.

11 Claims, 4 Drawing Sheets

METHYL 2,4,9-TRITHIAADAMANTANE-7-CARBOXYLATE

FIELD OF THE INVENTION

This invention relates to methyl 2,4,9-trithiaadamantane-7-carboxylate and a method for its manufacture.

BACKGROUND OF THE INVENTION

Growing an α-helical peptide from a substrate coated with a metallic film is known. An exemplary metallic film is made of gold, and the α-helical peptide is attached to the metallic film by a surface anchor. The anchor functions by chemically bonding with both the peptide and the film surface, thereby securing one to the other.

Prior-art anchors ordinarily bond to a metallic-film surface via a single sulfur-metal bond. In other words, prior-art anchors ordinarily have a single sulfur functionality that is reactive with a metallic-film surface. The deficiency of such anchors is that their resultant surface orientation is often uncontrollable and unpredictable. For example, their positioning is either substantially vertical or substantially parallel to the metallic-film surface. And that, in turn, directly impacts the, spatial orientation of an attached α-helical peptide. So if an anchor's spatial orientation is substantially parallel to a film surface, the attached α-helical peptide is also positioned substantially parallel to the film surface. Uncontrollable surface orientation is problematic because an α-helical peptide functions best as an optical switch when it is substantially vertical. The anchor's spatial orientation is therefore key.

In addressing the need for sulfur-based surface anchors having predictable surface orientation, the prior art teaches using a trithiaadamantane anchor to grow an α-helical peptide. Trithiaadamantane has a three-dimensional tripodal structure that provides more predictable surface orientation compared to single-sulfur anchors. Trithiaadamantane anchors form three sulfur-metal bonds with a metal surface, and that causes the compound to assemble in an upright vertical position. The anchor's upright surface orientation causes the α-helical peptide to likewise have a vertical spatial orientation, and that is preferred.

Prior-art trithiaadamantane anchors have previously been manufactured only by using the specific chemical intermediate- ethyl 2,4,9-trithiaadamantane-7-carboxylate. The prior art fails to provide useful alternate intermediates. A significant drawback to any method that employs ethyl-2,4,9-trithiaadamantane-7-carboxylate is that ethyl-2,4,9-trithiaadamantane-7-carboxylate can only be produced at the relatively low yield of about 10-25%.

So the art needs an alternate intermediate compound, one other than ethyl 2,4,9-trithiaadamantane-7-carboxylate, that can be used to produce trithiaadamantane anchors for growing α-helical peptides. There is also a need for an alternate intermediate compound that can be used in making trithiaadamantane anchors, wherein the alternate intermediate compound can be produced at a yield greater than the prior art's 10-25% yield for ethyl-2,4,9-trithiaadamantane-7-carboxylate. There is an additional need for methods directed to making trithiaadamantane anchors.

SUMMARY OF THE INVENTION

This invention provides a compound having the formula:

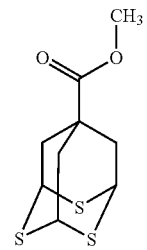

This invention further provides a method for synthesizing methyl 2,4,9-trithiaadamantane-7-carboxylate comprising the step of reacting oxidized methyl triallyl acetate with a sulphuring agent and a Lewis acid to produce methyl 2,4,9-trithiaadamantane-7-carboxylate.

Some advantages of this invention are that methyl 2,4,9-trithiaadamantane-7-carboxylate can be employed as a chemical intermediate in manufacturing compounds having trithiaadamantane anchors. Advantageously, methyl 2,4,9-trithiaadamantane-7-carboxylate is a drop-in replacement for ethyl-2,4,9-trithiaadamantane-7-carboxylate in methods for making compounds having trithiaadamantane surface anchors. A noted advantage over the prior-art intermediate, ethyl-2,4,9-trithiaadamantane-7-carboxylate, is that methyl 2,4,9-trithiaadamantane-7-carboxylate can be synthesized in a 35-40% yield, which is a clear improvement over the 10-25% yield of prior-art methods for producing ethyl-2,4,9-trithiaadamantane-7-carboxylate.

DETAILED DESCRIPTION OF THE INVENTION

Figure 1:
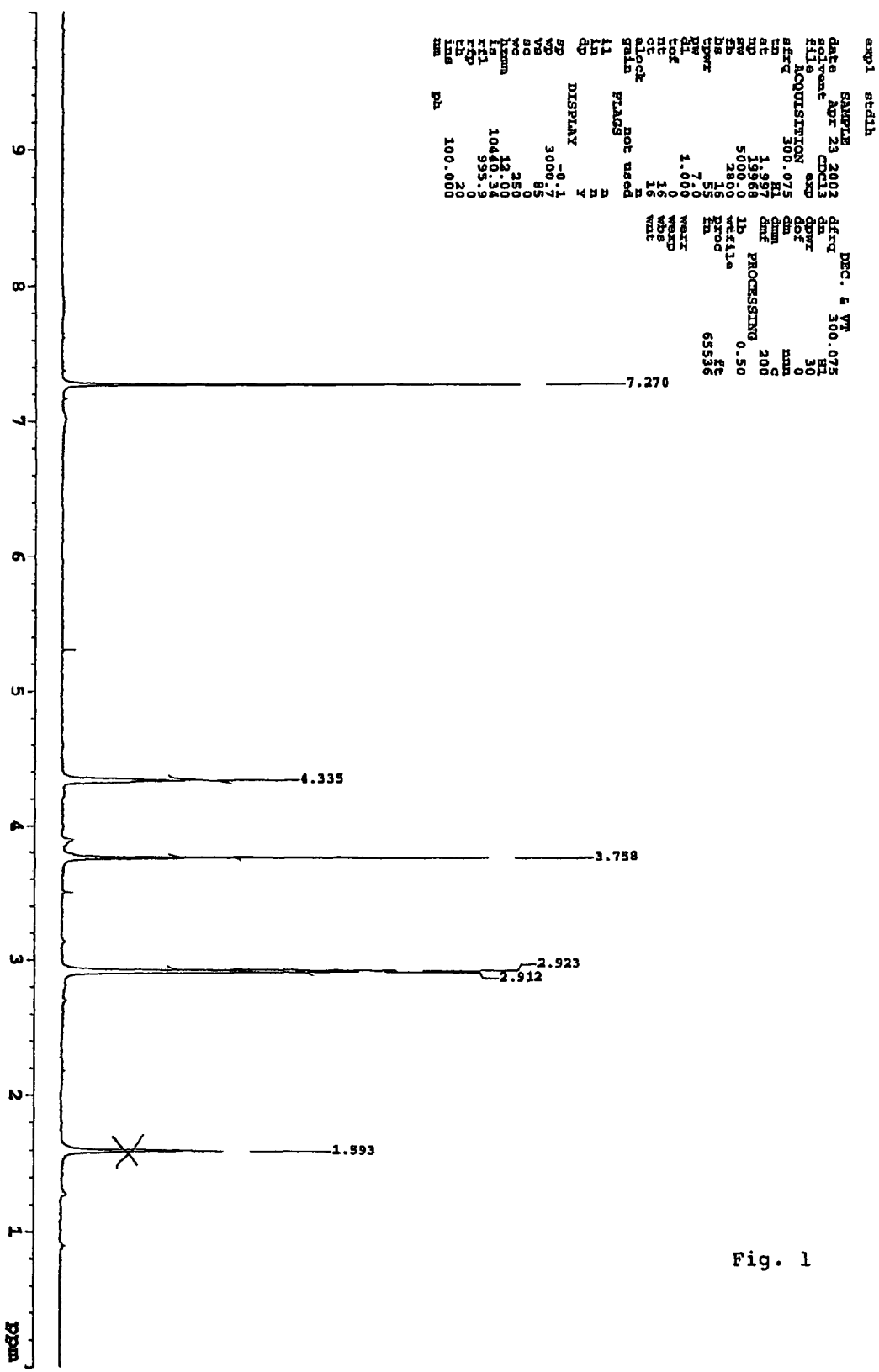
FIG. 1 is a $^1$H NMR spectrum of methyl 2,4,9-trithiaadamantane-7-acetate produced by the subject method.
Figure 2:
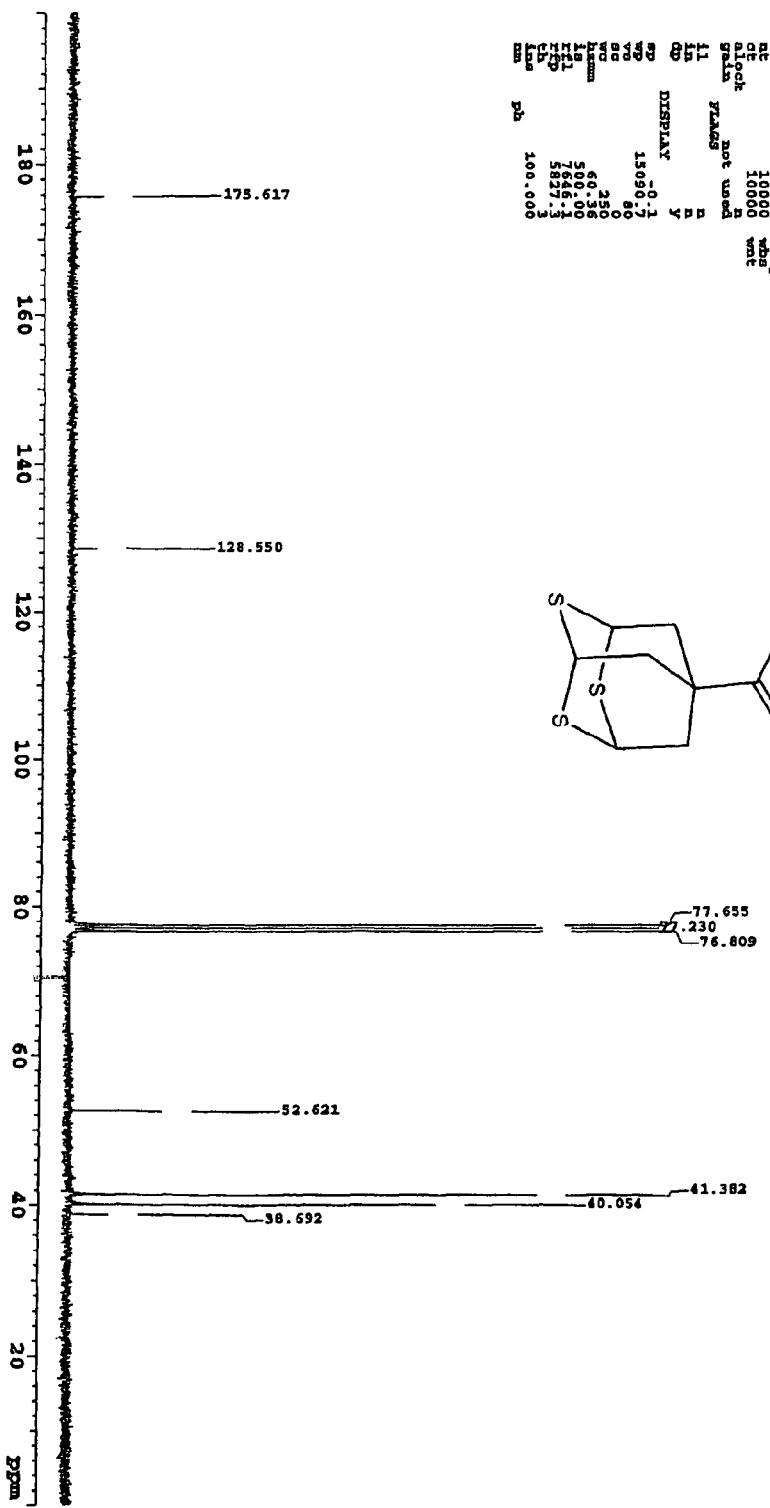
FIG. 2 is a $^1$H NMR spectrum of 2,4,9-trithiaadamantane-7-carboxylic acid produced by the subject method.
Figure 3:
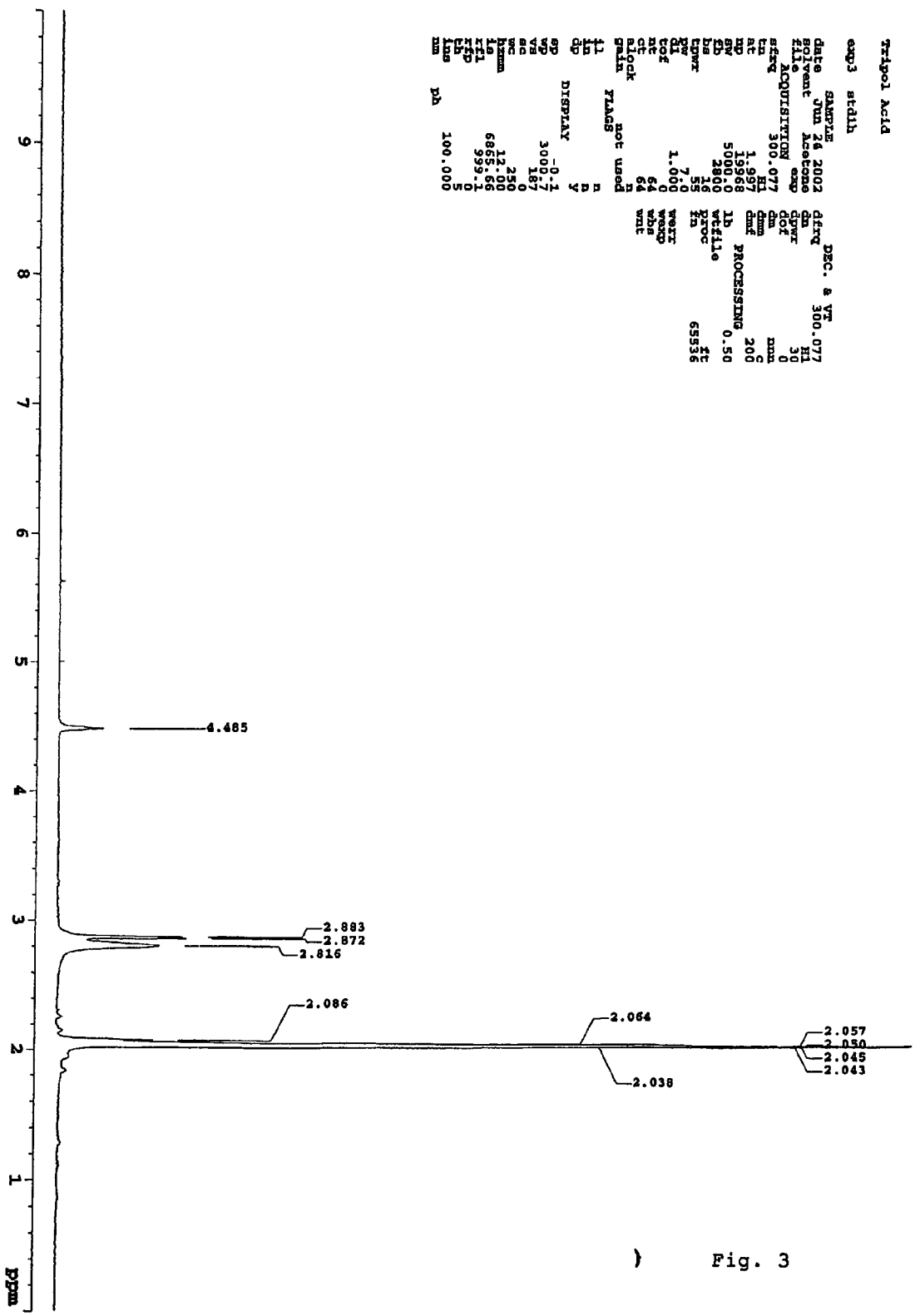
FIG. 3 is a $^{13}$C NMR spectrum of methyl 2,4,9-trithiaadamantane-7-carboxylate produced by the subject method.
Figure 4:
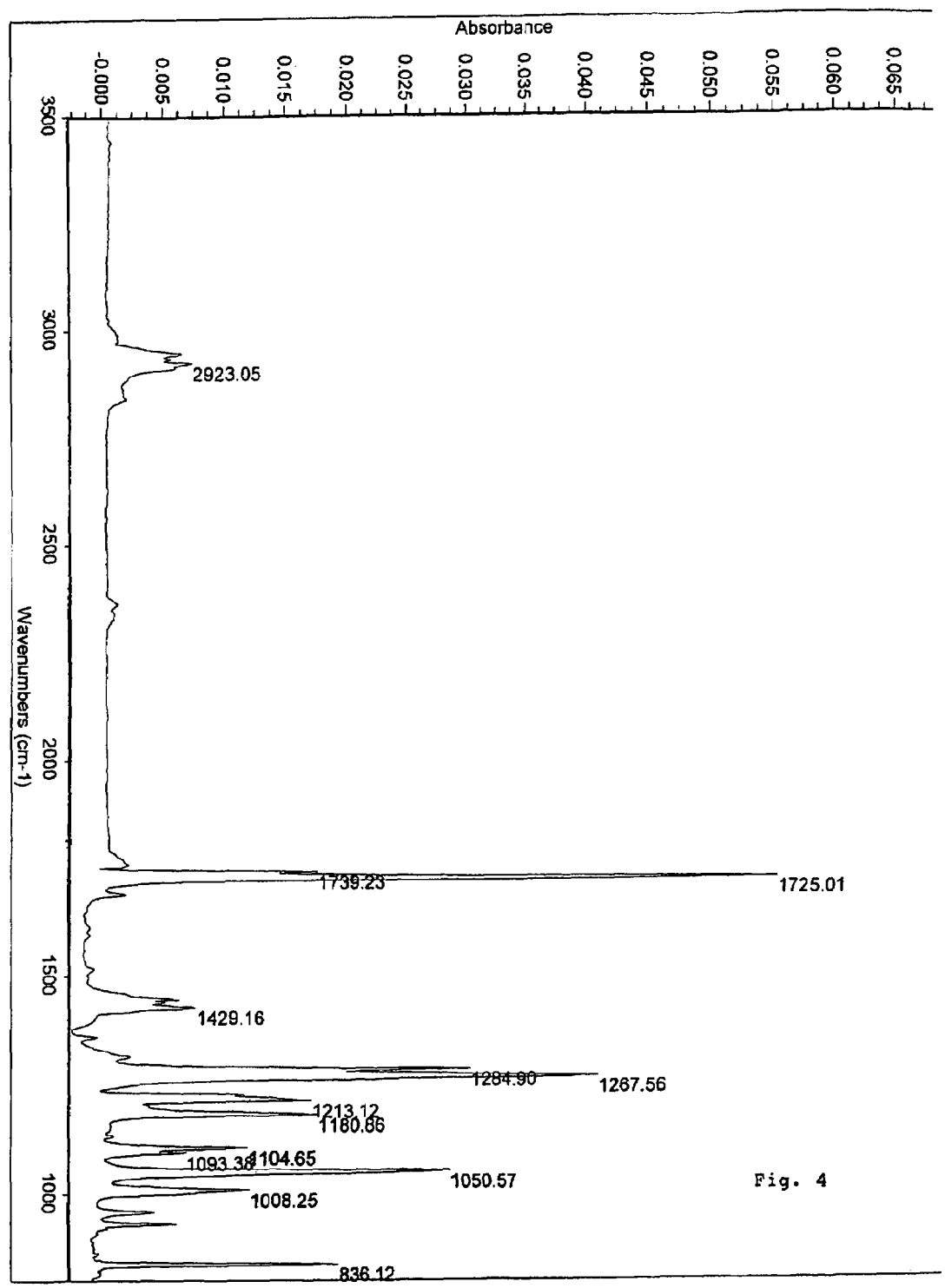
FIG. 4 is an IR spectrum of methyl 2,4,9-trithiaadamantane-7-carboxylate produced by the subject method.

This invention is generally directed to methyl 2,4,9-trithiaadamantane;-7-carboxylate and a method for its manufacture.

Methyl 2,4,9-trithiaadamantane-7-carboxylate is represented by the formula:

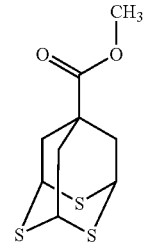

Methyl 2,4,9-trithiaadamantane-7-carboxylate is synthesized by reacting oxidized methyl triallyl acetate with a sulphuring agent and a Lewis acid. A general understanding of the method can be gained from the following simplified reaction scheme:

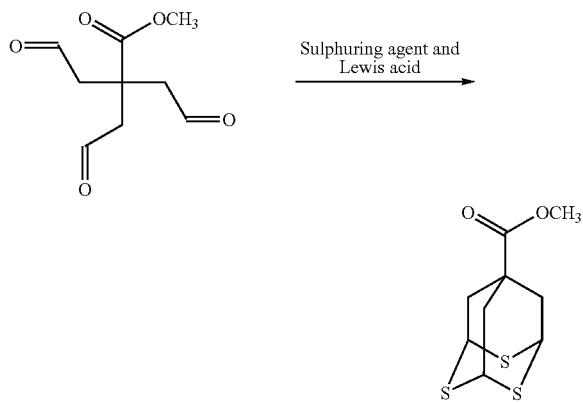

A nonlimiting example of this method adds Lawesson's reagent and $BF_3 \cdot Et_2O$ to oxidized methyl triallyl acetate. The reaction then proceeds under reflux for approximately 100 hours.

Oxidized methyl triallyl acetate is preferably synthesized, and that is accomplished by the oxidation of methyl triallyl acetate. Any known method of oxidation can be employed, but ozonolysis is preferred. Ozonolysis of methyl triallyl acetate can be performed by preparing a solution of methyl triallyl acetate in freshly-distilled methylenechloride followed by stirring and cooling the solution to −78° C. in a dry-ice acetone bath. Ozone is subsequently bubbled through the solution until a light-blue color persists. A simplified reaction scheme is provided:

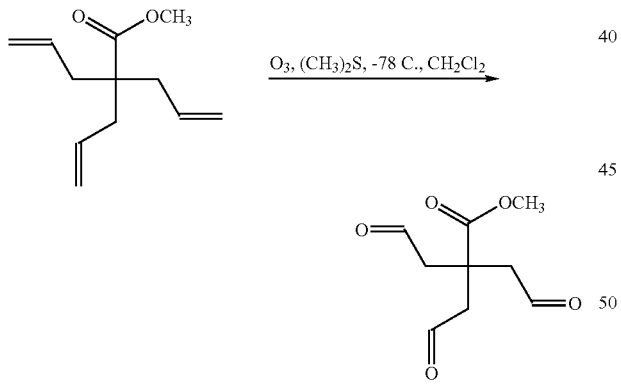

Any sulphuring agent can be employed in synthesizing methyl 2,4,9-trithiaadamantane-7-carboxylate. A sulfuring agent converts ketonic groups into thioketonic groups as represented by the reaction scheme:

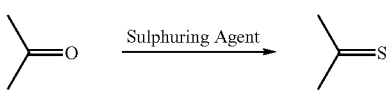

Preferred sulphuring agents include 2,4-bis(4-methoxyphenyl)-1,3,2,4-dithiadiphosphetane 2,4-disulfide (Lawesson's reagent); phosphorous pentasulfide hexamethyldisiloxane (PPHD); other suitable sulphuring agents; or any combination thereof.

The relative mole ratio of sulphuring agent to oxidized methyl triallyl acetate can generally range from about 6:1 to about 1:1. Preferably, the mole ratio ranges from about 3:1 to about 2:1.

Any Lewis acid can be employed in practicing the present invention. Lewis acids are well-known molecules, characterized as such for their ability to form a covalent bond with a second molecule by accepting a pair of electrons from the second molecule. Preferred Lewis acids include the complex of boron trifluoride and ethyl ether ($BF_3 \cdot Et_2O$), the complex of boron trichloride and ethyl ether ($BCl_3 \cdot Et_2O$), other suitable electron-pair acceptors, and any combination thereof.

The mole ratio of Lewis acid to oxidized methyl triallyl acetate preferably ranges from about 4:1 to about 1:1. More preferably, the mole ratio ranges from about 3:1 to about 2:1. Generally, the concentration of Lewis acid in the reaction medium ranges from about 0.5 to about 1.0 molar (M).

Any noncoordinated or weakly coordinated reaction solvent can be employed in synthesizing methyl 2,4,9-trithiaadamantane-7carboxylate. Nonlimiting examples of preferred solvents are methylene chloride ($CH_2Cl_2$), carbon tetrachloride ($CCl_4$), benzene, and combinations thereof. Effective amounts of non-coordinated or weakly coordinated solvent can be determined by a person of ordinary skill in the art without undue experimentation.

Synthesizing methyl 2, 4, 9-trithiaadamantane-7-carboxylate preferably occurs under reflux, and persons of ordinary skill in the art can determine the required temperature without undue experimentation.

EXAMPLES

In order to demonstrate practice of the present invention, the following examples have been prepared and tested. The examples should not, however, be viewed as limiting the scope of the invention. The claims will serve to define the invention.

Methyl 2,4,9-trithiaadamantane-7-carboxylate

A solution of 5 grams of methyl triallyl acetate in 100 milliliters freshly distilled methylenechloride was stirred and cooled to −78° C. in a dry-ice acetone bath. Ozone was bubbled through the cooled mixture until a light-blue color persisted. The ozone line was then disconnected and the excess ozone was removed by argon flow for 10 minutes. 6.0 grams dimethyl sulfide was added to the reaction mixture at −78° C. The mixture was slowly warmed up to room temperature. The mixture was then concentrated via rotary evaporation. To this mixture, 100 milliliters of methylenechloride, 28.0 grams of Lawesson's reagent, and 100 milliliters of neat $BF_3 \cdot Et_2O$ were added respectively. The mixture was then refluxed for 100 hours. Additional methylenechloride was added (100 mL). The mixture was washed using conventional techniques with 0.2 M potassium carbonate three times. The organic layer was dried over magnesium sulfate and evaporated. The resulting mixture was purified by column chromatography on silica gel using 30% methylenechloride in hexane to give pure methyl 2,4,9-trithiaadamantane-7-carboxylate (35-40% yield; melt point 149° C.-151° C.).

Purification of methyl 2,4,9-trithiaadamantane

Freshly prepared copper powder in water was decanted and washed with acetone to remove most of the water. Then the suspension of copper powder in acetone was washed with dry THF. The crude TPCOOMe sample was dissolved in THF and added into the suspension of copper powder in THF. The mixture was warmed to 40° C. for 8 hours while stirring rapidly. After filtration, the organic solution was concentrated under reduced pressure. The solid product of TPCOOMe was then recrystallized in THF/hexthane.

The copper powder was prepared by the method described by Keen, Keen, R. T. *Anal. Chem.* 1957, 29, 1039-1041, which is herein incorporated by reference. Typically, 20 g of copper sulfate was dissolved in 200 mL of diluted hydrochloric acid (20 mL of 2N hydrochloric acid in 200 mL of distilled water). 7 g zinc powder was suspended in 15 mL of distilled water containing a small amount of wetting agent. Then the slurry of zinc and water was added slowly to the copper sulfate solution. The mixture was stirred vigorously until the red-brown copper precipitated. The copper powder was washed carefully with distilled water for at least 5 times, covered with water, and stored below 0° C.

It should be evident that the present invention substantially improves the art by providing methyl 2,4,9-trithiaadamantane-7-carboxylate and a method for making it. While, in accordance with the patent statutes, only the preferred embodiments of the present invention have been described in detail hereinabove, the present invention is not to be limited thereby. Rather, the scope of the invention shall include all modifications and variations that fall within the scope of the attached claims.

What is claimed is:

1. A method for synthesizing methyl 2,4,9-trithiaadamantane-7-carboxylate comprising the step of:
    reacting oxidized methyl triallyl acetate with a sulphuring agent and a Lewis acid to produce methyl 2,4,9-trithiaadamantane-7-carboxylate.

2. The method of claim 1, wherein the sulphuring agent is 2,4-bis(4-methoxyphenyl)-1,3,2,4-dithiadiphosphetane 2,4-disulfide; phosphorus pentasulfide hexamethyl-disiloxane; or a combination thereof.

3. The method of claim 1, wherein the sulphuring agent is reacted with oxidized methyl triallyl acetate in a relative mole ratio ranging from about 6:1 to about 1:1.

4. The method of claim 1, wherein the sulphuring agent is reacted with oxidized methyl triallyl acetate in a relative mole ratio ranging from about 3:1 to about 2:1.

5. The method of claim 1, wherein the Lewis acid is BF3.Et2O, BCl3.Et2O, or a combination thereof.

6. The method of claim 1, wherein the Lewis acid is reacted with the oxidized methyl triallyl acetate in a relative mole ratio ranging from about 4:1 to about 1:1.

7. The method of claim 1, wherein the Lewis acid is reacted with the oxidized methyl triallyl acetate in a relative mole ratio ranging from about 3:1 to about 2:1.

8. The method of claim 1, wherein the step of reacting oxidized methyl triallyl acetate with a sulphuring agent and a Lewis acid to produce methyl 2,4,9-trithiaadamantane-7-carboxylate occurs in a noncoordinated or weakly coordinated solvent.

9. The method of claim 8 wherein the noncoordinated or weakly coordinated solvent is methylene chloride, carbon tetrachloride, benzene, or any combination thereof.

10. The method of claim 1, further comprising the step of using a metallic powder to purify a methyl 2,4,9-trithiaadamantane-7-carboxylate reaction product.

11. The method of claim 10, wherein the metallic powder is a copper powder.

\* \* \* \* \*